United States Patent [19]

Sugimura et al.

[11] Patent Number: 5,067,812
[45] Date of Patent: Nov. 26, 1991

[54] SYSTEMS FOR INSPECTING DEFECTS IN AN OPTICAL RECORDING MEDIUM

[75] Inventors: Koichi Sugimura; Fumio Kimura, both of Tokyo; Shigeru Izawa, Kanagawa, all of Japan

[73] Assignee: Kabushiki Kaisha CSK, Tokyo, Japan

[21] Appl. No.: 460,091

[22] PCT Filed: May 23, 1989

[86] PCT No.: PCT/JP89/00514
§ 371 Date: Jan. 23, 1990
§ 102(e) Date: Jan. 23, 1990

[87] PCT Pub. No.: WO89/11645
PCT Pub. Date: Nov. 30, 1989

[30] Foreign Application Priority Data
May 25, 1988 [JP] Japan .................. 63-128099

[51] Int. Cl.$^5$ ............................................. G01N 21/88
[52] U.S. Cl. ..................................... 356/237; 356/239
[58] Field of Search ......................... 356/71, 237, 239

[56] References Cited
U.S. PATENT DOCUMENTS
3,981,562  9/1976  Anthon .......................... 356/71 X
4,360,269  11/1982  Iwamoto et al. .................. 356/239
4,806,774  2/1989  Lin et al. ...................... 356/237 X FOREIGN PATENT DOCUMENTS
59-77051   5/1984  Japan .
62-124448  6/1987  Japan .

Primary Examiner—Vincent P. McGraw
Attorney, Agent, or Firm—Lackenbach Siegel Marzullo & Aronson

[57] ABSTRACT

The present invention provides a defect inspecting apparatus which can easily and accurately carry out the inspection of a defect in a recording medium and which does not require electrical image processing or image processing by means of software in order to eliminate a regular pattern.

This defect inspecting apparatus has an optical image forming system, such as a microscope, which enlarges an optical recording area of an optical recording medium having a regular pattern and an image processing part which converts the enlarged image sent from the optical image forming system into an image signal and detects the defect in the optical recording area from the image signal. In addition, a space filter which eliminates the space frequency component of the regular pattern is mounted on the optical image forming system.

5 Claims, 7 Drawing Sheets

FIG. 8
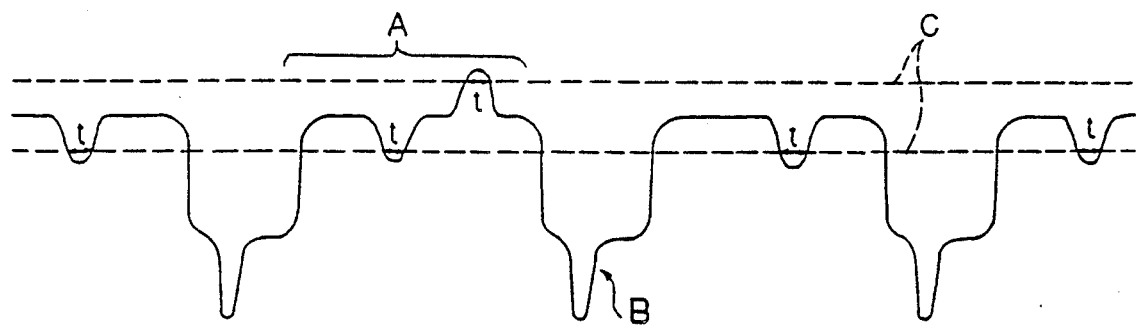
FIG.9A
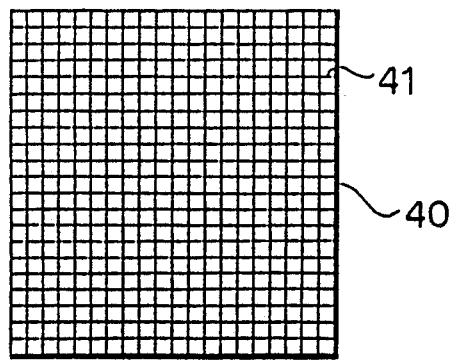
FIG.9C
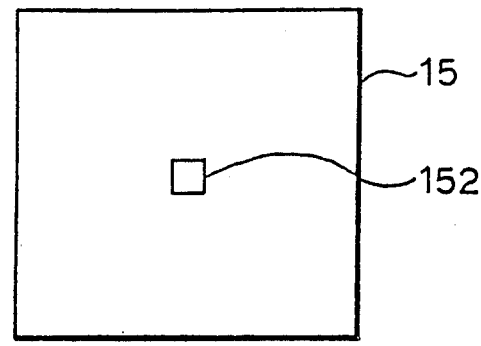
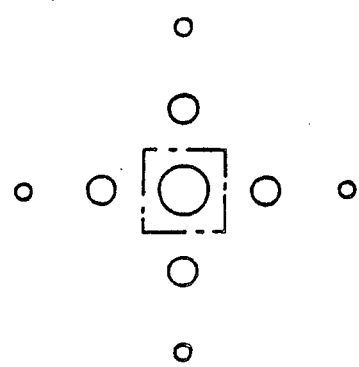
FIG.9B

SYSTEMS FOR INSPECTING DEFECTS IN AN OPTICAL RECORDING MEDIUM

BACKGROUND OF THE INVENTION

1. Field of the Invention

The present invention relates to a defect inspecting apparatus detecting defects such as cracks in an optical recording area of an optical recording medium having a regularly disposed regular pattern.

2. Description of the Related Art

In optical recording media such as an optical card accessing data by means of a laser beam, malfunctions at the time of data access are prevented by carrying out an inspection as to whether defects such as cracks are present in the optical recording area or not before actually writing data on or using the optical recording area.

Hitherto, although the inspection of the optical recording area of this type has been carried out by means of optical instruments such as a microscope, there are problems in that the inspection requires much labor and accurate results can not be obtained.

SUMMARY OF THE INVENTION

An object of the present invention is to provide a defect inspecting apparatus which solves the above described problems; that is the present invention easily and accurately carries out the inspection. In addition, the present invention does not require electrical image processing or image processing by means of software in order to eliminate the regular pattern.

The defect inspecting apparatus of the present invention which accomplishes the above object comprises an image forming optical system which enlarges an optical recording area of an optical recording medium having a regular pattern and an image processing part which converts the enlarged images obtained by the image-forming optical system into an image signal and detects the defect in the optical recording area by means of an image signal, and a space filter which removes the space frequency component of the regular pattern mounted on the image forming optical system.

More preferably, the space filter comprises an optical slit whose shape corresponds to the regular pattern.

According to the defect inspecting apparatus of the present invention, since the defect inspection can be carried out under the condition that the regular pattern present in the optical recording area is eliminated, the inspection can be easily and accurately executed.

Furthermore, since the regular pattern is optically eliminated, electrical image processing or image processing by means of software in order to eliminate the regular pattern are not required and thus the structure of the defect inspecting apparatus of the present invention can be simplified.

BRIEF DESCRIPTION OF THE DRAWINGS

FIG. 8 shows an image signal;

FIGS. 9 (A), (B) and (C) show other embodiments of the space filter, respectively.

DESCRIPTION OF THE PREFERRED EMBODIMENT

One embodiment of the present invention will be explained in detail with reference to the figures as follows.

FIGS. 1 to 8 explain one embodiment of the present invention.

Figure 1:
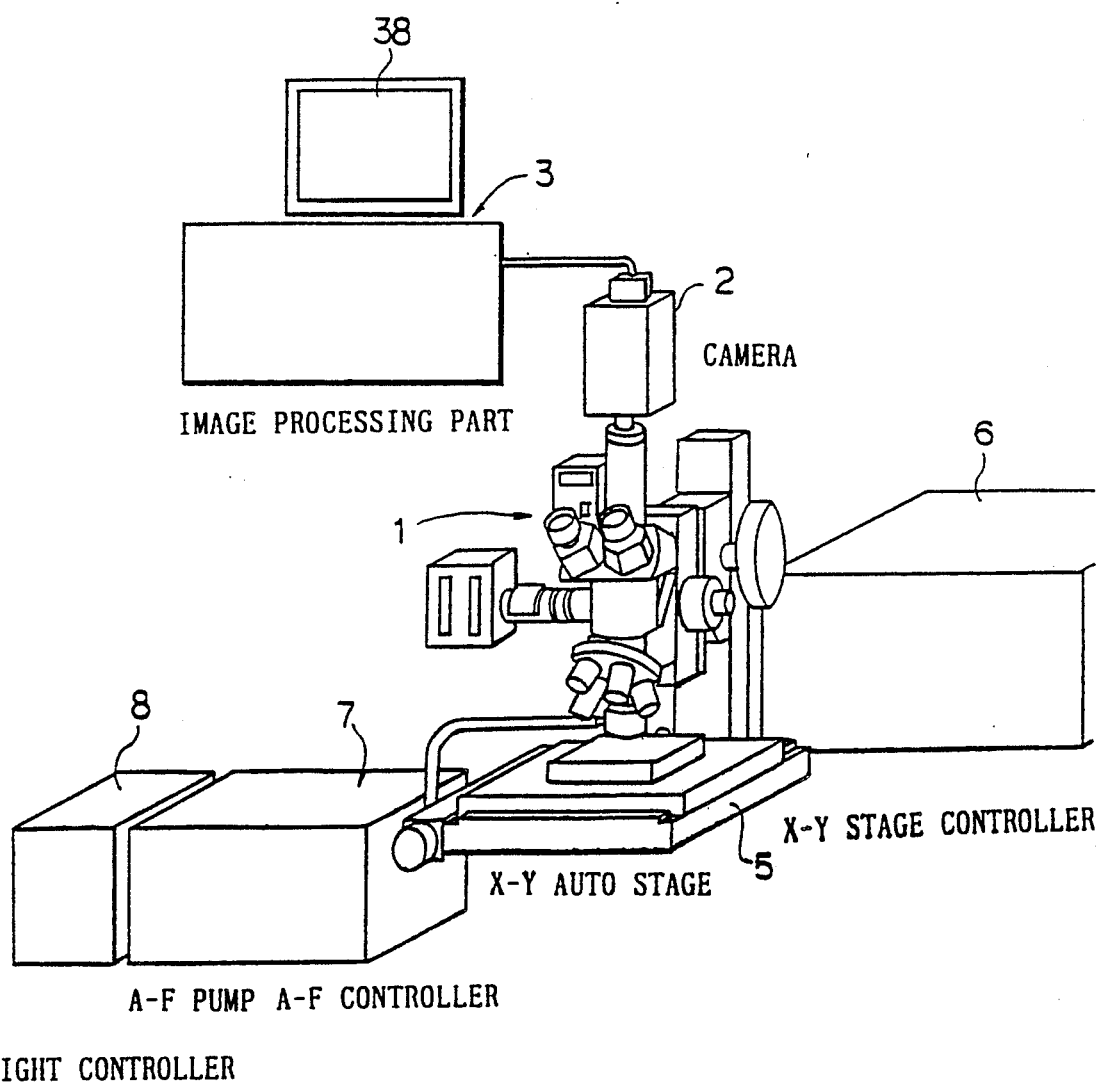
FIG. 1 is a general view of a defect inspecting apparatus of one embodiment of the present invention.

As shown in FIG. 1, the defect inspecting apparatus of the present invention comprises a microscope 1 as an image forming optical system which enlarges an optical recording area 40 (FIG. 3) of an optical memory card 4, an optical recording medium, a camera 2 and an image processing part 3.

An X-Y autostage 5 which carries the optical memory card 4, a stage controller 6 controlling the X-Y autostage 5, a focusing device 7 and a light controller 8 are attached to the microscope 1 described above.

Figure 2:
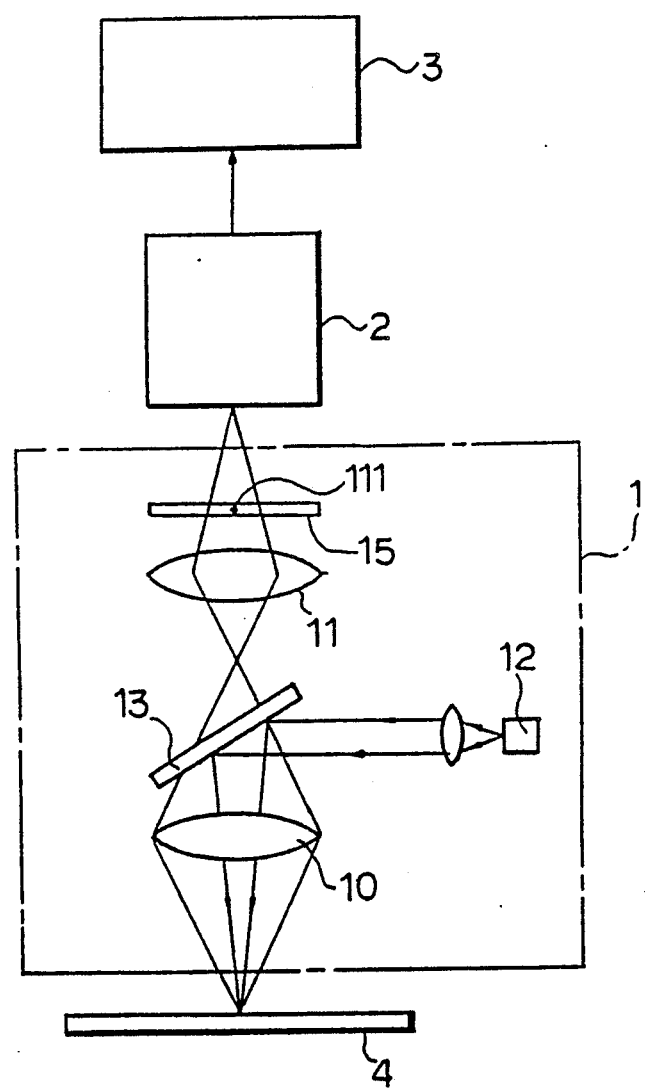
FIG. 2 is a block diagram of the parts of a microscope.
Figure 3:
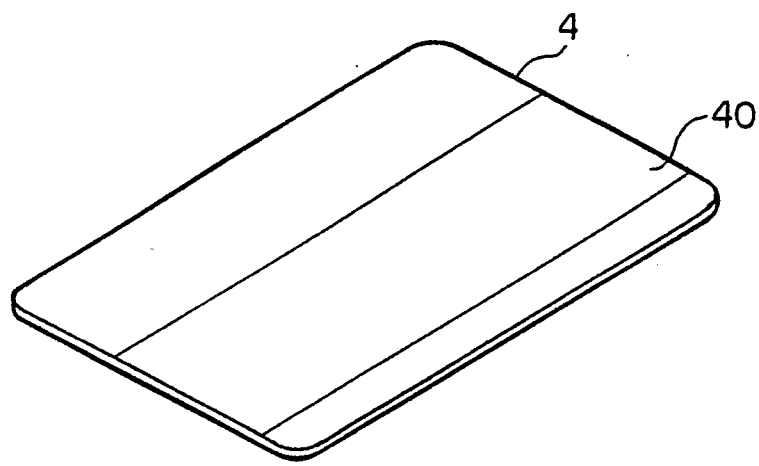
FIG. 3 is a perspective view of an optical memory card.

As shown in FIG. 2, the microscope 1 has an objective lens 10, a relay lens (the eyepiece) 11, a light source 12, a beam splitter 13 and a space filter 15. The light source 12 illuminates a visual field. The enlarged image of the optical memory card 4 formed by the microscope 1 is image-formed in the camera 2 by means of the relay lens (the eyepiece) 11.

Figure 6A:
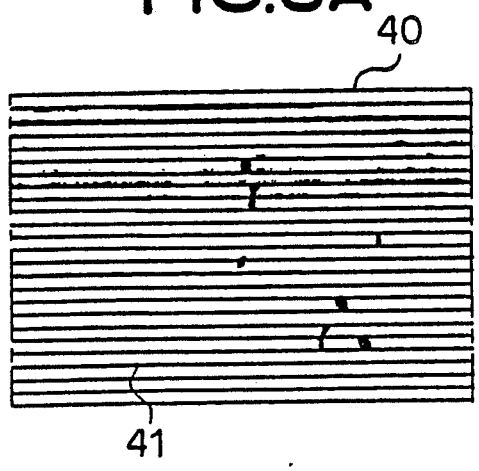
FIGS. 6 (A) and (B) show an optical recording area and an image-formed example obtained by the microscope, respectively.
Figure 6B:
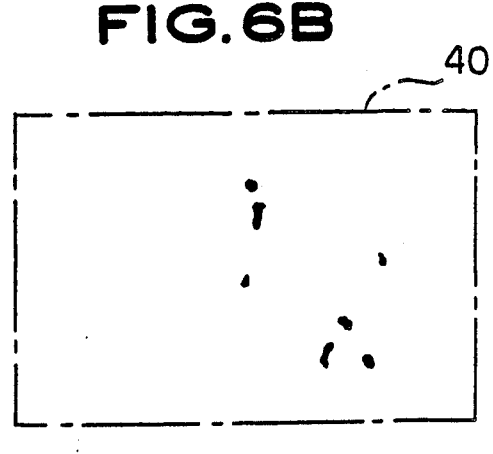

The space filter 15 is installed in order to eliminate only regular patterns 41, such as a track guide or a clock guide, etched on an optical recording area 40 of the optical memory car 4 at constant intervals, as shown in FIGS. 6 (A) and (B), from the image formed surface of the optical memory card 4 formed by the microscope 1.

Figure 4:
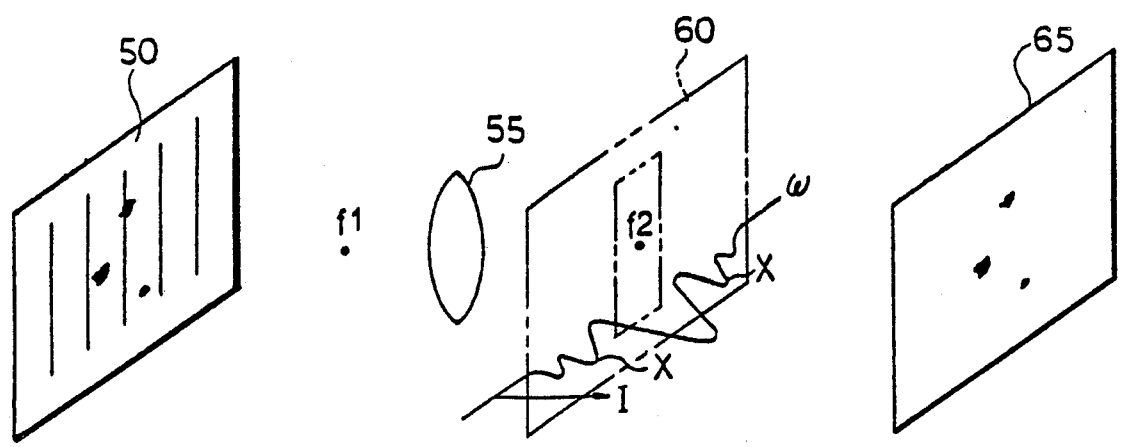
FIG. 4 shows the principle concerning the function of a space filter.

The principle concerning the function of the space filter 15 will be explained with reference to FIG. 4. The above described regular pattern 41 has a strong spectrum around a specific space frequency. When an image of a sample surface 50 having a regular pattern similar to the regular pattern 41 is formed by means of a lens 55, the space frequency is Fourier transformed at the second focusing position f2 (f1 is a first focusing position) of the lens 55 and the space frequency distribution shown in FIG. 4 is obtained. Letters I and ω designate strength and frequency, respectively. A part designated by a letter X is a space frequency component corresponding to the spectrum of the regular pattern. Thus, the space frequency components of the regular patterns converge to a position deviating from the center point.

Therefore, when a space frequency component X is cut by disposing a space filter 60 having a slit of a specified width at the second focusing position of the lens 55, an image formed surface 65 from which the regular pattern is eliminated will be obtained. The width of the slit is determined in accordance with the width of the regular pattern.

Figure 5A:
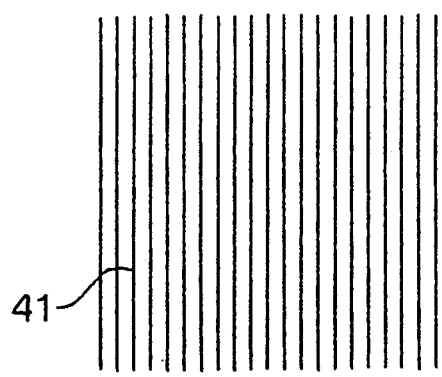
FIGS. 5 (A) and (B) show the regular pattern present in an optical recording area and a space filter, respectively.
Figure 5B:
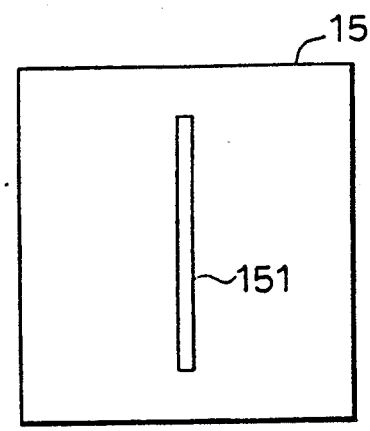

In this embodiment, the space filter 15 is installed in the second focusing position 111 (see FIG. 2) of the relay lens (the eyepiece) 11 of the microscope 1. In addition, one slit 151 is formed in the space filter 15 in correspondence to the regular pattern 41 of the optical memory card 4, as shown in FIGS. 5 (A) and (B). The space frequency components of the regular pattern 41 are reliably cut by controlling the width of this slit 151 in correspondence to the intervals of the regular pattern 41.

When the optical recording area 40 of the optical memory card 4 is enlarged by means of the aforementioned microscope 1, the enlarged image of the optical recording area 40 is obtained with the regular pattern 41 being eliminated. At this time, only the regular pattern 41 is eliminated as shown in FIGS. 6 (A) and (B), and it is needless to say other irregular patterns caused by such as cracks are enlarged just like that and the image is formed.

Figure 7:
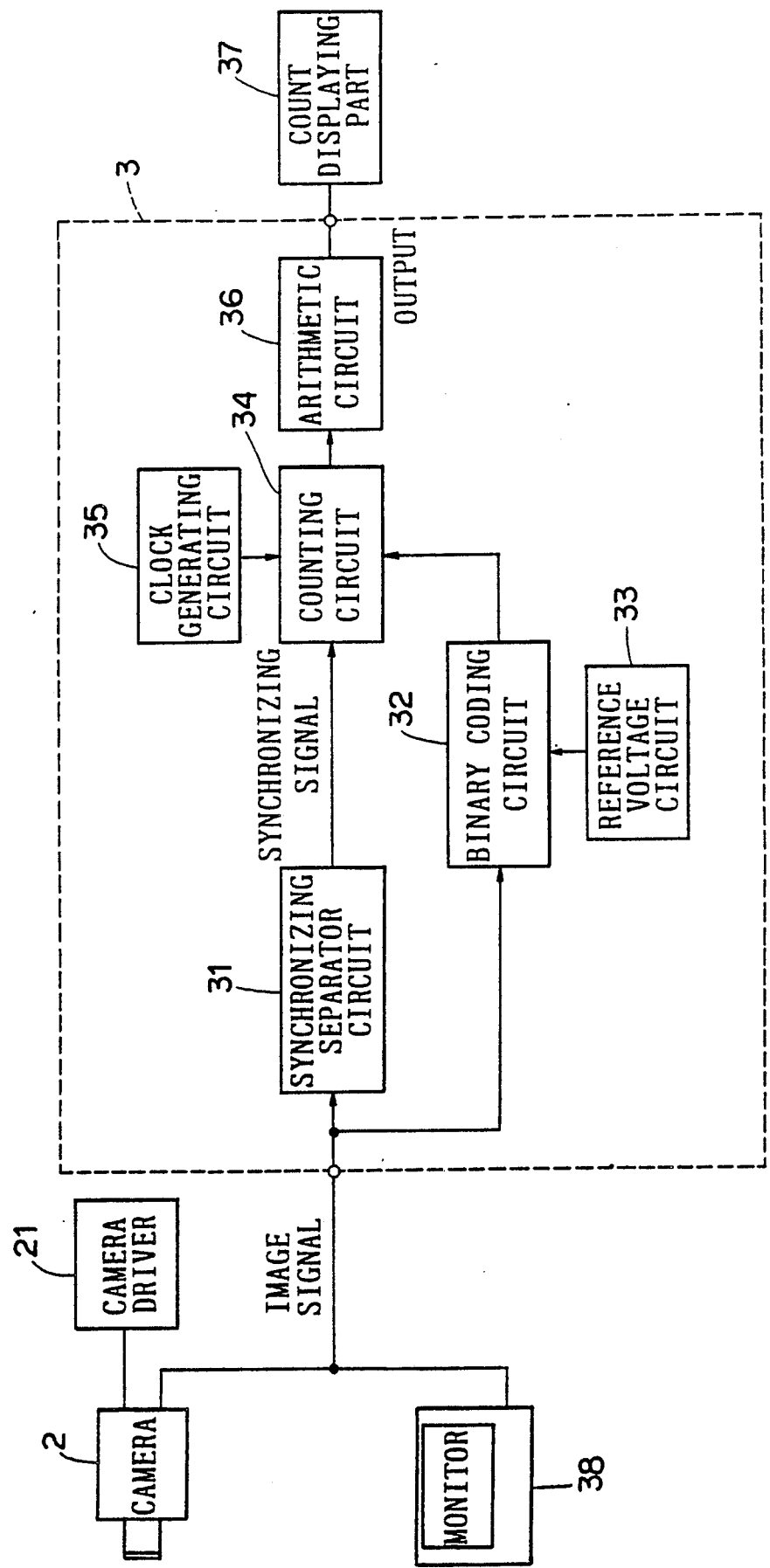
FIG. 7 is a block diagram of an image processing part.

The image processing part 3 comprises a synchronizing separator circuit 31, binary coding circuit 32, a reference voltage circuit 33, a counting circuit 34, a clock generating circuit 35, an arithmetic circuit 36 and a count displaying part 37, as shown in FIG. 7. An output terminal of the camera 2 is connected to the synchronizing separator circuit 31 of the image processing part 3. A numeric 21 designates a camera driver. A monitor 38 is connected to the camera 2 at the input side of the image processing part 3.

This image processing part 3 calculates a ratio (defect rate) of the defects (a crack, an alien and so on) against the optical recording area 40.

The synchronizing separator circuit 31 separates the image signal sent from the camera 2 into a vertical synchronizing signal and a parallel synchronizing signal, picks out the synchronizing signal, and outputs it to the counting circuit 34. The binary coding circuit 32 compares the voltage of the image signal to the reference voltage sent from the reference voltage circuit 33 and binarizes the image signal.

The reference voltage circuit 33 generates a reference voltage (binarizing level). The counting circuit 34 is timed by means of the synchronizing signal and counts the binarized signal of the image signal by means of a sampling cycle.

The clock generating circuit 35 generates a clock having the sampling cycle. The arithmetic circuit 36 calculates the defect rate based on the counting result obtained by the counting circuit 34. The count displaying part 37 digitally displays the defect rate calculated and obtained by the arithmetic circuit 36.

Subsequently, the operation of the thus constructed defect inspecting apparatus will be explained.

At first, the optical memory card 4 to be inspected is carried on the X-Y autostage 5 and the microscope 1 is controlled by means of the focusing device 7 and the light controller 8.

The enlarged image of the optical recording area 40 from which the regular pattern 41 is eliminated by the above described space filter 15 shines into the camera 2. This image is converted into the image signal by means of the camera 2. One example of the image signal at this time is shown in FIG. 8. In this figure, letters A and B designate a brightness signal of one scanning line and the synchronizing signal, respectively.

When no defect is present in the optical recording area 40, the brightness signal A varies in the almost constant range, but when the defects are present, the brightness signal A varies in the abnormal range.

The image signal of the camera 2 is sent to the synchronizing separator circuit 31 of the image processing part 3 and to the binary coding circuit 32.

A synchronizing signal B is isolated from the image signal by means of the synchronizing separator circuit 31 and obtained synchronizing signal B is sent to the counting circuit 34.

Comparison between the brightness signal A of the image signal and the reference voltage is carried out by the binary coding circuit 32 and the brightness signal A is binarized. That is, a binarized level C is set by the reference voltage circuit 33 in the image signal as shown in FIG. 8, and the binarized signal is generated corresponding to the time of the part exceeding the binarized level C.

The counting circuit 34 is timed by means of the synchronizing signal B and counts the binarized signal sent from the binary coding circuit 32 by means of the sampling sinchronization sent from the clock generating circuit 35.

The arithmetic circuit 36 calculates the sum of the time t of the part of the counting value obtained by the counting circuit 34 which exceeds the binarized level C and calculates the ratio of areas of the defect against the total area of the optical recording area as the defect ratio. Finally, the defect ratio is digitally displayed by the count displaying part.

The image signal is sent from the camera 2 to the monitor 38 and the enlarged image of the optical recording area is projected. Therefore, the condition of the optical recording area 40 can be directly confirmed by this projected image. Since the image projected to this monitor 38 is the image in which the regular pattern 41 is eliminated, the visual observation of the defect is easily carried out.

The position of the defect makes it possible to confirm its location by displaying positioning information sent from the X-Y autostage with the count displaying part 37 and the monitor 38.

Figure 10A:
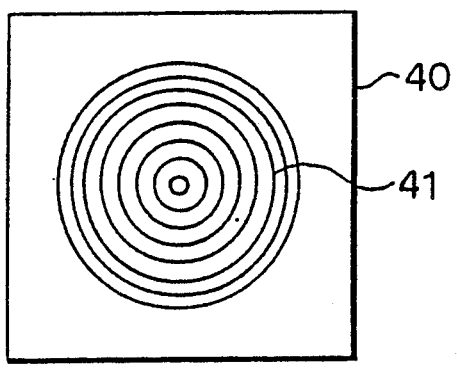
FIGS. 10 (A), (B) and (C) show other further embodiments of the space filter, respectively.
Figure 10C:
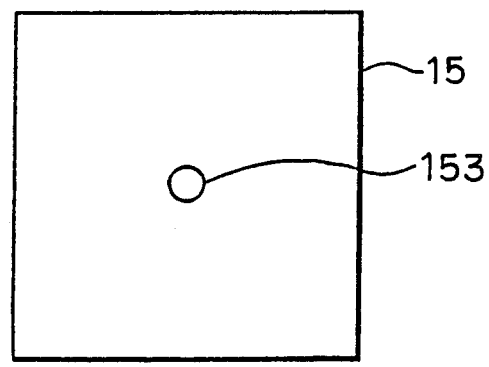
Figure 10B:
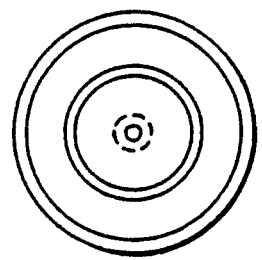

In the above described embodiment, the slit 151 is mounted on the space filter 15 in correspondence with the regular pattern 41 of the optical recording area 40. However, it is limited to the slit 151. For example, since the spectrum is distributed as shown in FIG. 9 (B) when the regular pattern 41 is lattice-shaped as shown in FIG. 9 (A), a square-shaped hole 152 is mounted on the space filter 15 as shown in FIG. 9 (C). Since the spectrum is distributed as shown in FIG. 10 (B) when the regular pattern 41 is concentric circular-shaped as shown in FIG. 10 (A), a circular-shaped hole 153 is mounted on the space filter 15 as shown in FIG. 10 (C).

Although the case inspecting an optical memory card 4, as the optical recording medium is described, it is needless to say that it can be applied to another optical recording medium such as an optical disc.

What is claimed is:

1. A defect inspecting apparatus comprising: an image forming optical system for enlarging an optical recording area of an optical recording medium having a regular pattern including a camera, an objective lens for forming an enlarged image of an optical recording area and a relay lens means for image forming an enlarged image in the camera means: an image processing portion for converting an enlarged image in said camera enlarged by said image forming optical system into an image signal and detecting a defect in said optical recording area from said image signal; and a slotted space filter mounted on the optical axis between said camera and said relay lens in said image forming optical system for eliminating a space frequency component of said regular pattern.

2. A defect inspecting apparatus according to claim 1 wherein said space filter is constructed with an optical slit wherein said optical slit which has a shape corresponding to the shape of said regular pattern.

3. A defect inspecting apparatus according to claim 1 wherein said optical slit is square-shaped when said recording medium has a lattice-shaped regular pattern.

4. A defect inspecting apparatus according to claim 1 wherein said optical slit s circular-shaped when said recording medium has a concentric circular-shaped regular pattern.

5. A defect inspecting apparatus according to claim 1 wherein said image processing portion has a synchronizing separator circuit for receiving a signal from said camera and, a counting circuit, a clock generating circuit and an arithmetic circuit arranged to provide a digital display output corresponding to defects in the recording area.

* * * * *